United States Patent
Hutchings

[19]
[11] Patent Number: 5,899,963
[45] Date of Patent: * May 4, 1999

[54] SYSTEM AND METHOD FOR MEASURING MOVEMENT OF OBJECTS

[75] Inventor: Lawrence J. Hutchings, Castro Valley, Calif.

[73] Assignee: Acceleron Technologies, LLC, Oakland, Calif.

[*] Notice: This patent is subject to a terminal disclaimer.

[21] Appl. No.: 08/877,342

[22] Filed: Jun. 17, 1997

Related U.S. Application Data

[63] Continuation-in-part of application No. 08/570,759, Dec. 12, 1995, Pat. No. 5,724,265.

[51] Int. Cl.$^6$ ............................................. G01C 22/00
[52] U.S. Cl. .................. 702/145; 702/141; 702/142; 702/149; 702/146; 364/143
[58] Field of Search ............... 340/323 R, 384.71; 235/105; 364/143, 410.1; 128/779; 482/3, 8, 74, 902; 342/52; 324/171; 377/24.5, 24.2; 73/490; 702/101, 149, 141–142, 146, 147, 166

[56] References Cited

U.S. PATENT DOCUMENTS

| | | | |
|---|---|---|---|
| 3,789,402 | 1/1974 | Heywood et al. | 340/384.71 |
| 3,797,010 | 3/1974 | Adler et al. | 340/323 R |
| 3,865,305 | 2/1975 | Sampey | 377/24 |
| 4,053,755 | 10/1977 | Sherrill | 702/160 |
| 4,094,199 | 6/1978 | Holdren et al. | 73/514.22 |
| 4,180,726 | 12/1979 | DeCrescent | 250/222.1 |
| 4,220,996 | 9/1980 | Searcy | 702/160 |
| 4,312,358 | 1/1982 | Barney | 600/483 |
| 4,334,190 | 6/1982 | Sochaczevski | 324/171 |
| 4,371,945 | 2/1983 | Karr et al. | 702/160 |
| 4,387,437 | 6/1983 | Lowrey et al. | 702/160 |
| 4,449,191 | 5/1984 | Mehnert | 702/94 |
| 4,460,823 | 7/1984 | Ruehlemann | 235/105 |
| 4,560,861 | 12/1985 | Kato et al. | 235/105 |
| 4,571,680 | 2/1986 | Wu | 702/160 |
| 4,578,769 | 3/1986 | Frederick | 702/160 |
| 4,627,011 | 12/1986 | Spencer et al. | 701/70 |
| 4,630,226 | 12/1986 | Tanaka | 702/103 |
| 4,703,445 | 10/1987 | Dassler | 702/160 |
| 4,736,312 | 4/1988 | Dassler et al. | 702/160 |
| 4,741,008 | 4/1988 | Franke | 378/53 |
| 4,763,287 | 8/1988 | Gerhaeuser et al. | 702/160 |
| 4,787,051 | 11/1988 | Olson | 364/518 |
| 4,821,218 | 4/1989 | Pötsch | 73/514.01 |
| 4,855,942 | 8/1989 | Bianco | 702/160 |
| 4,885,710 | 12/1989 | Hersberger et al. | 702/146 |
| 5,033,013 | 7/1991 | Kato et al. | 702/160 |
| 5,117,444 | 5/1992 | Sutton et al. | 377/24.2 |
| 5,181,181 | 1/1993 | Glynn | 702/141 |
| 5,206,652 | 4/1993 | Hoyt et al. | 342/52 |

(List continued on next page.)

OTHER PUBLICATIONS

Herbert Goldstein, "Classical Mechanics" Harvard University, Addison–Wesley Publishing, 1959.

AGARD, "Inertial Navigation Systems and Components"A-GARD Conference Proceedings No. 43, NATO, 1968.

Kenneth R. Britting, "Inertial Navigation Systems Analysis" Massachusetts Institute of Technology, Wiley–Interscience 1971.

*Primary Examiner*—James P. Trammell
*Assistant Examiner*—Cuong H Nguyen
*Attorney, Agent, or Firm*—Sofer & Haroun, LLP

[57] ABSTRACT

A device that measures the distance traveled, speed, and height jumped of a moving object or a person while running or walking. Accelerometers and rotational sensors are placed in the object or in the sole of one shoe, or in a wrist watch or the waist of the user, along with an electronic circuit that performs mathematical calculations to determine the distance and height. A microprocessor calculates an output speed based upon step-distance and elapsed time, and the distance traveled from the sum of all previous steps. The output of the microprocessor is coupled to a display that shows the distance traveled, speed, or height jumped.

35 Claims, 7 Drawing Sheets

U.S. PATENT DOCUMENTS

| | | | |
|---|---|---|---|
| 5,245,537 | 9/1993 | Barber | 364/410.1 |
| 5,396,510 | 3/1995 | Wilson | 372/38 |
| 5,452,216 | 9/1995 | Mounce | 701/214 |
| 5,471,405 | 11/1995 | Marsh | 702/41 |
| 5,516,334 | 5/1996 | Easton | 482/8 |
| 5,524,637 | 6/1996 | Erickson | 600/592 |
| 5,574,669 | 11/1996 | Marshall | 702/149 |
| 5,583,776 | 12/1996 | Levi et al. | 701/217 |

5,899,963

SYSTEM AND METHOD FOR MEASURING MOVEMENT OF OBJECTS

CROSS-REFERENCE TO RELATED APPLICATIONS

This application is a continuation-in-part of application Ser. No. 08/570,759 entitled SYSTEM AND METHOD FOR MEASURING MOVEMENT OF OBJECTS filed by Lawrence J. Hutchings on Dec. 12, 1995, now U.S. Pat. No. 5,724,265, the contents of which are incorporated herein by reference.

FIELD OF THE INVENTION

This invention relates generally to the field of measuring instruments and is particularly directed to a system and method for determining the speed, distance and height traversed by a person or an object while in motion.

BACKGROUND OF THE INVENTION

In recent years many individuals have turned to their own fitness program of regular jogging. As used herein, jogging is also intended to include running and walking and the words are used interchangeably. Jogging has long been recognized for its therapeutic effects on the body. It purportedly increases cardiopulmonary fitness, helps to lower blood pressure, decreases cholesterol and triglyercides associated with heart disease and reduces weight. Jogging is also one of the easiest exercises to do. It requires no athletic ability and can be done almost any time and any place with a minimum of equipment and without assistance. In more recent times, jogging has also gained acceptance for its recreational value as well and is recognized as a positive factor in promoting psychological well-being.

The popularity of jogging today is well documented by the large numbers of products and literature available to the public. As in many exercise and sporting endeavors, there exists in the prior art a wide variety of devices for aiding those who jog. Many people who run, jog or walk regularly desire to know their progress over time. Therefore, it is desirable to know the accurate distance and speed traveled during an exercise session. This information allows a jogger to monitor his or her progress and accordingly pursue a regular course of exercise designed to enhance performance.

Further, it has become desirable to accurately measure the speed of amateur and professional runners, both in training and during competition. In the prior art, such measurements were made with a stop watch timing the runner over a known distance. Heretofore, it has not been possible to obtain accurate instantaneous speeds of runners or height jumped using the measuring devices currently known in the prior art.

The simplest jogging aids for measuring movements are basic pacing timers such as those disclosed in U.S. Pat. No. 3,540,344 to Veech and U.S. Pat. No. 3,882,480 to Greber. Pacing timers generate a repetitive audio tone signal at selected intervals for pacing the strides of the jogging, where the length of the interval between tones is adjusted to suit the pace of the individual jogger.

There are other running aids known in the prior art such as pedometers as disclosed in U.S. Pat. No. 4,053,755 to Sherrill. These devices usually count the number of steps taken and for a particular stride length, the approximate distance traversed can be determined.

Human speedometers and odometers that measure the speed and distance traveled by a person include devices that utilize ultrasound to measure the distance between each foot such as disclosed in U.S. Pat. No. 4,736,312 to Dassler. Also used is a device that measures the elapsed time of shoe in contact with the ground and converts this to the length of step and speed as disclosed In U.S. Pat. No. 4,578,769 to Frederick.

While pacing timers, pedometers, ultra sound, and elapsed foot-time-distance devices are useful to the runner and walker, they are deficient in several areas. For example, while ultra sound devices can measure the distance between two feet, this is not equivalent to the length of a step or a stride, which is defined as the distance traveled by the same foot from the beginning of a stride till the end of the same stride. For example, the difference between (1) separation between feet, as measured by the ultra sound device, and (2) stride length, is different for each person and will vary for different speeds of running.

Furthermore, devices that employ elapsed-foot-contact-time measurements, have significant errors in measuring stride length. It is known that above a certain speed, stride length begins to increase as speed increases, and the relationship of stride length to speed is not directly proportional, and moreover, is different for each runner. In addition, most of the devices mentioned above require calibration, which may prove to be a difficult task. For example, many of these devices need to be calibrated by the manufacturer or by specially designed equipment.

It is, therefore, a difficult task to determine the correct stride length for an individual runner at various speeds. Thus, pacing timers can provide no more than a constant running pace, and pedometer measurements are only useful as an approximation of distance traversed. Also, ultra sound and elapsed-foot-time-distance devices provide only a rough approximation of actual distance traveled and speed of the person. Also, none of the prior art includes a measurement of height jumped. Running and walking aids known in the prior art are often deficient and cumbersome to use and they often add weight to the runner or walker while providing only marginal utility in terms of the amount of information available and its accuracy.

With the foregoing in mind, the ideal running aid should, therefore: be light in weight; serve a number of useful functions; be inexpensive; provide measurements that are readily available to the user; be reliable and easy to use; and provide accurate measurements of speed, distance traversed, height jumped, and other useful information.

OBJECT OF THE INVENTION

It is the overall objective of this invention to provide a new and improved running and walking measuring system, which overcomes the disadvantages of the prior art devices and substantially increases the amount and accuracy of information available to the jogger.

A specific objective of this invention is to provide a new and improved running and walking measuring system, in which the speed of the runner can be easily and accurately determined.

A further specific objective of this invention is to provide a new and improved running and walking measuring system, in which the distance traversed by the runner can be easily and accurately determined.

Another specific objective of this invention is to provide a new and improved running measuring system, in which the height jumped by the runner or jogger can be easily determined.

A still further objective of this invention is to provide a new and improved running and walking measuring system having the above advantages which is light in weight, relatively inexpensive and convenient to use.

SUMMARY OF THE INVENTION

In accordance with one aspect of the invention, a device for measuring the performance of a runner utilizes accelerometers and rotational sensors to measure the speed, distance traveled, and height jumped of a person. It may be preferably placed in the sole of a shoe and information signals may be transmitted to the user's watch for display. An indication signal may be configured to reset measurement values to zero coordinates with each step taken, and the system records accelerations relating to the movement of the foot to the next step. The accelerations and angels of rotation of the foot recorded are transformed to a reference frame of the ground, and integrated twice to obtain displacement of each step. Time is incorporated with the acceleration to perform the integration. Once the length of steps is determined, the elapsed time is used to obtain the speed of the person, and the sum of the step lengths is used to obtain the distance traveled. The maximum value of the vertical displacement is used to determine the height jumped. One set of three-component linear accelerometers and one set of three-component rotational sensors may be employed to resolve the absolute motion of a person from the motion of the foot.

According to another aspect of the invention, substantially satisfactory measurements may be obtained with two accelerometers and one rotational sensor; or the system may be attached to the top portion of the user's shoe, instead of installation inside the sole of the shoe.

In accordance with another embodiment of the invention, the measuring system may be located at any part of the body, such as the waist or the wrist of the user, instead of the shoe. In order to alleviate the measurement errors caused by employing the measuring system at different parts of the body, the system sets a reference frame that maintains the same orientation during a predetermined cycle. The accelerometers and the rotational sensors employed by the measuring system, measure the distance traveled by the user. Preferably, in order to alleviate the effects of gravitational field on the accelerometers, the system initiates a new cycle at a time when the velocity of the user is constant and the measured acceleration is influenced substantially by gravity.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof may best be understood by reference to the following detailed description when read with the accompanying drawings in which:

DETAILED DESCRIPTION OF THE INVENTION

Figure 1:
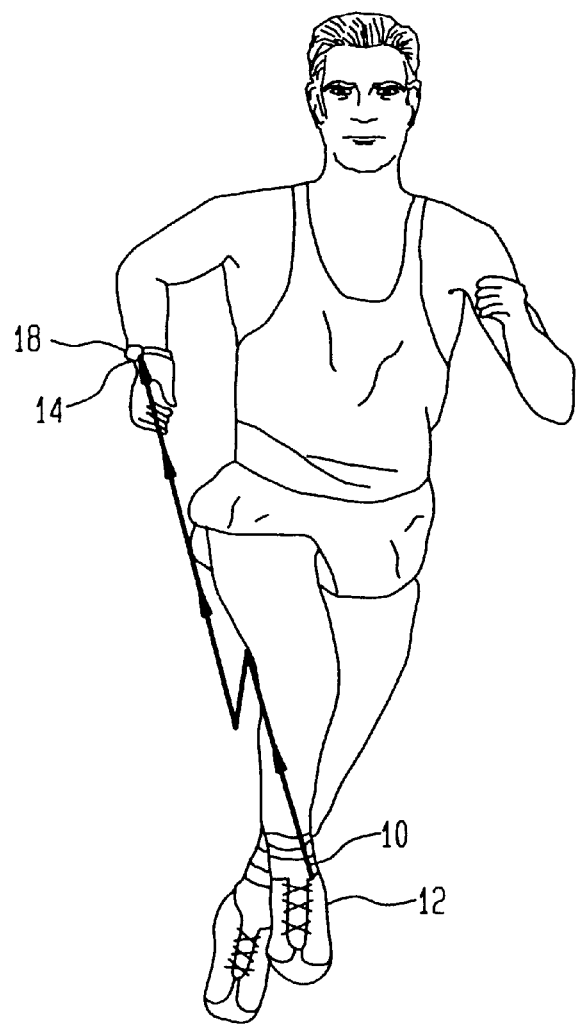
FIG. 1 illustrates one embodiment of the invention as employed by a user.

FIG. 1 shows an embodiment of a measuring system 10 as employed by a user, although the invention is not limited in scope to the location of different components of the system as illustrated herein. For example, the components of the measuring system may be located at other parts of the body, such as the wrist and the waist area. In accordance with the embodiment illustrated in FIG. 1, the shoe of the user may include interrelated elements such as linear accelerometers; rotational sensors; a microprocessor to calculate the distance and height of each step; a foot impact switch; battery; and a radio transmitter 12, as will be explained in more detail below.

As shown in FIG. 1, the user may wear a hand display having a radio receiver 14. The radio receiver may alternately be located at a remote site so that the performance of the runner can be monitored by another person. Incorporated into the receiving unit may be a microprocessor for processing the received signals into the speed of the runner, the distance traversed and the height jumped. The processed information may be selectively displayed on display 18. The hand display may also perform other functions, for example, it may selectively display normal watch functions, such as time of day, date, alarm and stop watch signals.

Figure 2:
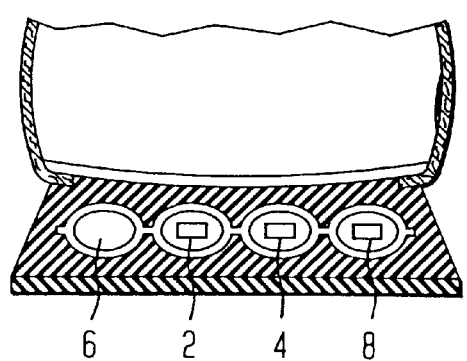
FIG. 2 illustrates the location of the system's components in the sole of the shoe, in accordance with an embodiment of the invention.

FIG. 2 shows one possible location of different components of the measuring system in the sole of the user's shoe. However, the invention is not limited in scope in this respect, and various components of the system in accordance with the present invention may be implemented in a variety of arrangements. Accelerometers 2, rotational sensors 4 and a contact switch 8 are preferably placed in the ball-of-the-foot portion of the sole of the shoe so that they may come in contact with the ground for each step during either walking or running. As it will explained in more detail below, the measuring system in accordance with the present invention may also operate without contact switch 8. Measuring system 10 may include three rotational sensors 4, each configured to measure the angle of the user's foot with respect to a reference frame as will be explained in more detail below. Rotational sensors 4 are well known, such as those provided by AMP model numbers ACH-04-08. Each rotational sensor converts the measured angle into a corresponding signal, which is employed by a microprocessor 6 to calculate information related to the user's movements, such as user's speed, distance traveled and the height jumped. It will be appreciated that the present invention is not limited in scope to the components illustrated in FIG. 2. For example, instead of contact switch 8, other means may be employed so as to generate a signal to indicate the beginning of each step.

Measuring system 10 preferably includes three accelerometers 2, each configured to measure the acceleration of the user's foot with respect to a reference frame as will be explained in more detail below. The accelerometers may also be located in the sole of the user's shoe. Accelerometers 2 are well known, such as those provided by Analog Devices model ADXL05. Each accelerometer may convert the measured acceleration into a corresponding signal, which may be preferably employed by microprocessor 6 to accomplish movement measurements.

Also, other components may be separated and placed in another portion of the shoe. For example, the measuring system may be placed at another location of the shoe or another location in the body of the user.

Figure 3:
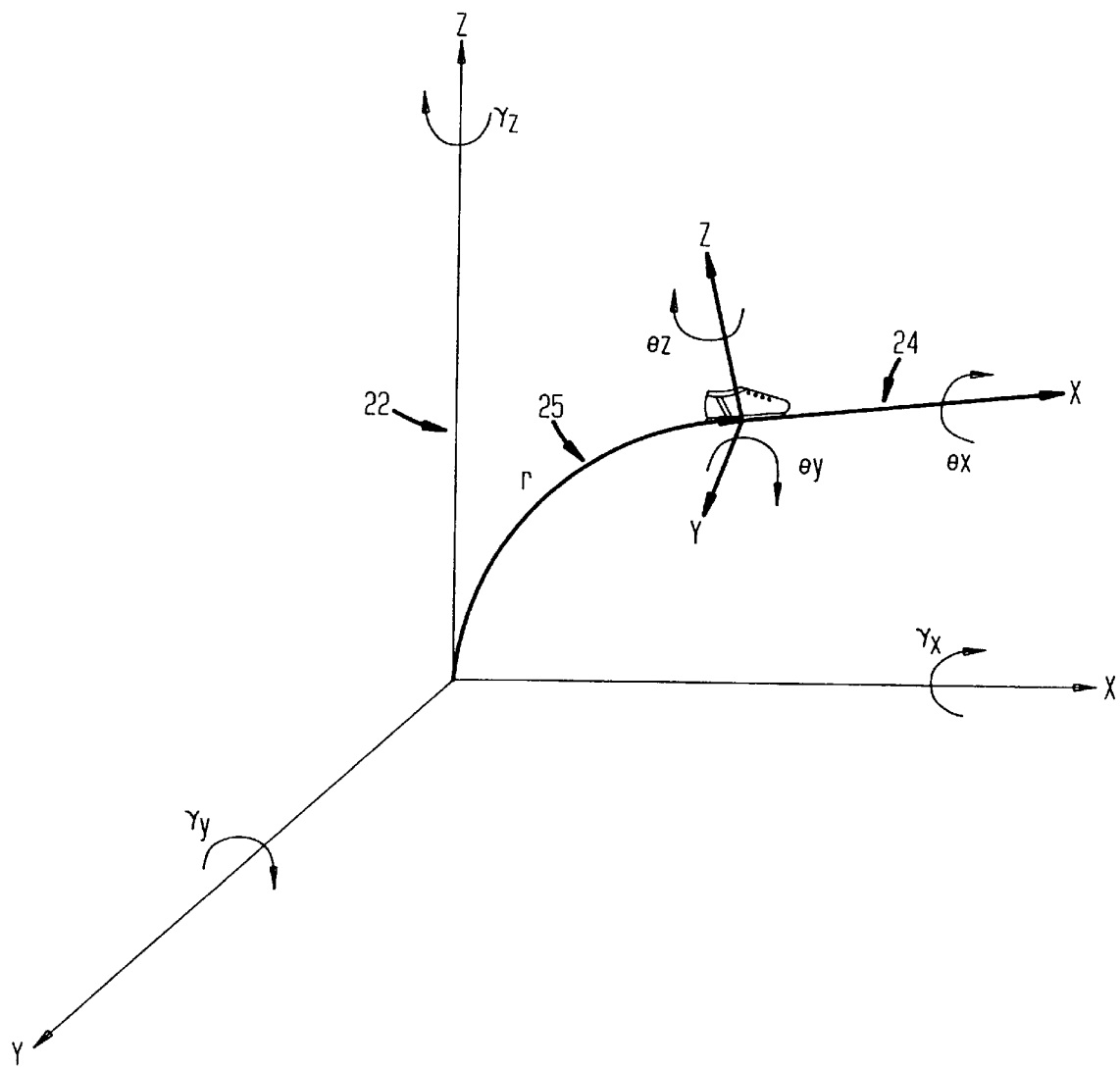
FIG. 3 is a coordinate system for the reference frame of the stationary ground, and the vectors of linear and rotational motion that are necessary to determine motion of the foot in accordance with one embodiment of the invention.

FIG. 3 illustrates a plot of the coordinate systems necessary to resolve step length and height. In the present context, a first coordinate system, such as (x, y, z) 22, is referred to as the reference frame coordinate system of the stationary ground. ($\gamma_x$, $\gamma_y$, $\gamma_z$) are the rotational coordinates about the x, y and z axis of the reference frame. In one embodiment of the invention, rotation about the z axis may not be measured. These values advantageously indicate the slope of the ground at the beginning of the step. Preferably, the reference frame coordinate system is reset at the initiation of a new step and remains stationary throughout the time the same foot leaves and touches the ground again. The orientation of the reference frame coordinate system with respect to the foot is arbitrary, but it is preferably selected so that at the beginning of the step the positive x direction may be aligned with the axis of the sole of the shoe, the positive y axis may be in the same plane as the sole and at right angles to the x axis, and the positive z axis may be normal to the plane of the sole of the shoe. The arrows in FIG. 3 indicate the direction of positive motion. The length and height of each step with respect to this coordinate system may be measured in accordance with the present invention as explained in more detail hereinafter.

FIG. 3 also illustrates a second coordinate system, such as (x, y, z) 24, referred to as the translational coordinate system of the linear accelerometers. This coordinate system moves with the foot and may be centered at the location of the sensors. FIG. 3 further illustrates rotational coordinates, such as ($\theta_x$, $\theta_y$, $\theta_z$) about the axes X, Y and Z. These rotational coordinates may be employed advantageously to keep track of the orientation of the (X, Y, Z) coordinate system relative to the (x, y, z) coordinate system, as will be explained below, and to resolve the accelerations along the reference frame.

In FIG. 3, an exemplary foot is shown part way through a step that moves along a trajectory r such as 25. The orientation of the translational coordinate system with respect to the foot is the same as described for the reference frame, but moves with the foot. Preferably, the reference and translational coordinate systems may be aligned together every time a new step is initiated. Furthermore, in accordance with another embodiment of the invention as explained in reference with FIGS. 7–9, the orientation of the reference frame and the translational coordinate system may be aligned at a beginning of a cycle which may comprise more than one step.

Figure 4:
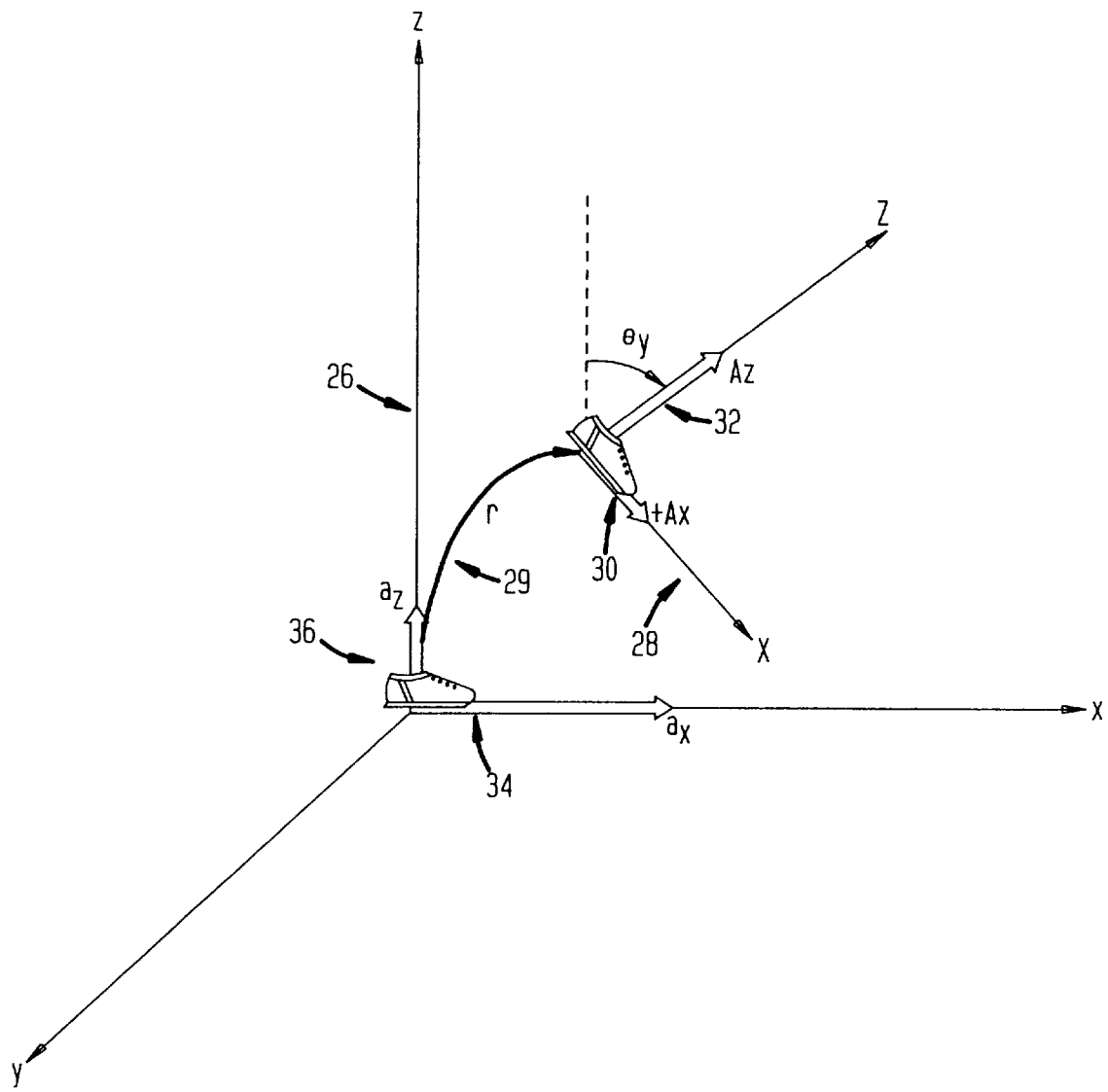
FIG. 4 is a side view diagram of the foot during running, illustrating information employed to resolve step length in two dimensions in accordance with one embodiment of the invention.

FIG. 4 illustrates an example of a motion of the foot and how the length of the step is resolved for a motion in one plane, along two dimensions (here, the plane of the paper), and for a step along a horizontal surface. The reference frame coordinate system 26 is that described as 22 in FIG. 3, and the translational coordinate system 28 is that described as 24 in FIG. 3. The foot is shown part way through a step having moved along trajectory r such as 29. The translational coordinate system is moving along trajectory r 29, as described in FIG. 3.

FIG. 4 also illustrates acceleration vectors (Ax, Az) in the translational coordinate system. These accelerations are represented by arrows aligned along the X and Z axes of the translation coordinate system, respectively. The length of the arrows represent the amount of acceleration for each component (30 and 32, respectively). The angle of rotation about the y axis relative to the reference frame coordinate system is $\theta_y$. From these components of motion the acceleration relative to the reference frame coordinate system can be resolved. This is shown as ax and az in the reference frame (34 and 36, respectively).

The amount of acceleration and its direction (a vector solution) is preferably employed to keep track of forward and reverse motions of the foot. For example, if motion remains in the (z,x) plane and the surface is horizontal (FIG. 4), then $$ax = Ax \cos \theta_y + Az \sin \theta_y \quad (1)$$

$$az = -Ax \sin \theta_y + Az \cos \theta_y - g \quad (2)$$

Where g is the acceleration due to gravity, which is preferably considered as a factor due to the use of accelerometers. This follows because typically the accelerometers that may be employed by the measuring system are of the type that are affected by gravity. However, the invention is not limited in that scope. For example, if an accelerometer that is not influenced by gravity is employed then the g factor in equation (2) may be omitted.

Gravity may be assumed to be a constant as explained in more detail below. Here, acceleration az is assumed to be vertical and aligned with the orientation of gravity. However, the invention is not limited in that scope. For example, acceleration az may be aligned at an angle from the direction of gravity, such as on a hill, as explained in more detail below. The −g factor added to the az component of equation (2) is to balance the effect of gravity on the accelerometers. For example, if the user of the system is standing still, $\theta_y=0$ and Az=+g, then az=0. If the user is moving up at g, Az will read 2g, and az=g. If the user moves down at g and $\theta_y=180$, Az=0, and az=−g. For forward horizontal motion, with, for example, $\theta_y=45°$, Az and Ax would be positive and substantially equal from motion, but there would be an added positive component g $\cos\theta_y$ added to Az and an added negative g $\sin \theta_y$ component added to Ax, and their sum would be such that az=0. The length of the step is obtained by integration as discussed in reference with FIG. 5.

Figure 5:
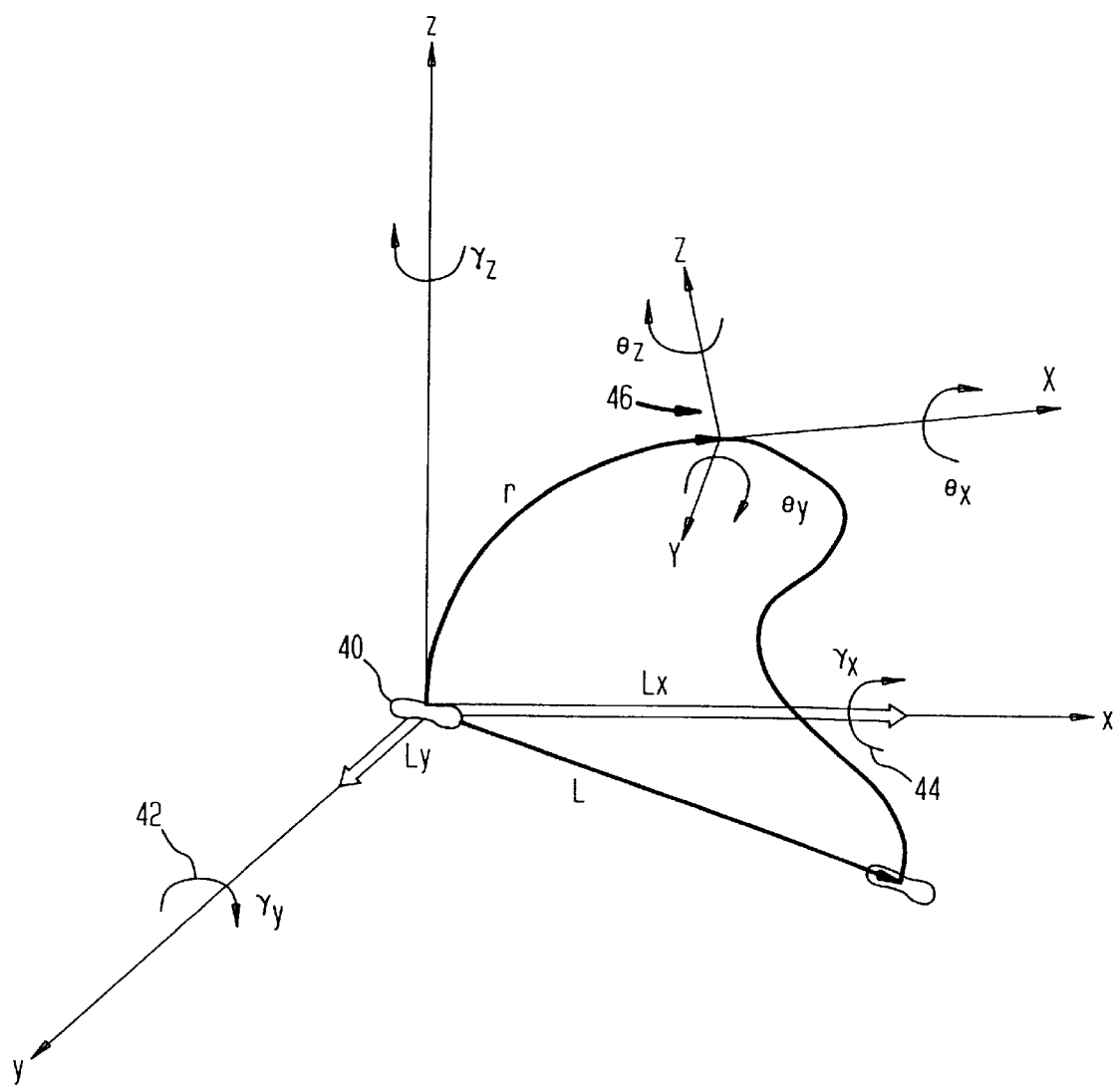
FIG. 5 is a vector diagram illustrating output acceleration, velocity and displacement of one embodiment of the invention during running.

FIG. 5 shows the elements that may be employed to obtain a complete solution of the foot motion in three dimensions. The reference frame is established from the foot contact at the beginning of a step 40. However the invention is not limited in scope in that respect, and in accordance with other embodiments of the invention, the reference frame may be established in other manners as explained in more detail below and in reference with FIGS. 7–9.

The reference frame z axis may be chosen such that it is not aligned with gravity. For example, the reference frame z axis may not be aligned with the direction of gravity if the ground (x,y plane) is not horizontal. $\gamma_y$ 42 is the angle of the x axis from the horizontal plane, and $\gamma_x$ 44 is the angle of the y axis from the horizontal plane. These values are unknown, as they depend on the orientation of the reference frame in relation to the gravity, such as for example, the slope of the ground at the beginning of each step, and are calculated by measuring system 10, as explained below. At any point along the trajectory r, the components of motion in the reference frame can be determined from the linear accelerometers and rotational sensors in the translational coordinate system 46.

$$ax = AxC_1 - AyC_2 + AzC_3 - g \sin \gamma_y \quad (3)$$

$$ay = AxC_4 + AyC_5 - AzC_6 - g \sin \gamma_x \quad (4)$$

$$az = -AxC_7 + AyC_8 + AzC_9 - g \cos \gamma_x \cos \gamma_y \quad (5)$$

Where the $C_1$–$C_9$ are transformation coefficients that are determined from the output signals generated by translation and rotation sensors. These signals represent, for example, the angles θ or incremental changes in the angles θ, shown in FIG. 5. In accordance with another embodiment of the invention, the angles may be determined from rotation sensors that either measure rotation angles of the embodiment, such as with rotation accelerometers or measure rotations relative to the reference coordinate system directly, such as with magnetic field sensors. There are several methods established in prior art to determine the values of the coefficients, such as described by Britting, Kenneth R. *Inertial Navigation Systems Analysis,* Wiley-Interscience, a Division of John Wiley & Sons, Inc. (1971 Library of Congress no. 70-168635) and incorporated herein by reference; Goldstein, Herbert *Classical Mechanics,* ch. 4, Addison Wesley Publishing, Reading Mass. (1956) and incorporated herein by reference.

In accordance with one embodiment of the invention, an exemplary solution to equation (3) though equation (5) employs the angles ($\theta_x$, $\theta_y$, $\theta_z$) as shown in FIGS. 3–5 and described in more detail in Van Bronkhorst, A. *Euler Angle Strapped-Down Computer,* Advisory Group for Aerospace Research and Development (AGARD), Inertial Navigation Systems and Components, North Atlantic Treaty Organization (May 1968) and incorporated herein by reference. To this end, the components of motion in the reference frame can be determined as follows:

$$ax = [\cos \theta_x \cos \theta_y \cos \theta_z - \sin \theta_x \sin \theta_z]Ax - [\sin \theta_x \cos \theta_y \cos \theta_z + \cos \theta_x \sin \theta_z]Ay + \sin \theta_y \cos \theta_z Az \quad (6)$$

$$ay = [\cos \theta_x \cos \theta_y \sin \theta_z + \sin \theta_x \cos \theta_z]Ax - [\sin \theta_x \cos \theta_y \sin \theta_z - \cos \theta_x \cos \theta_z]Ay + \sin \theta_y \sin \theta_z Az \quad (7)$$

$$az = -\cos \theta_x \sin \theta_y Ax - \sin \theta_x \sin \theta_y Ay + \cos \theta_y Az \quad (8)$$

As explained in reference with FIG. 4, the terms involving gravity g counteract the accelerations in gravity recorded by the linear accelerometers. The values for $\gamma_x$ and $\gamma_y$ may be determined at the initiation of each step, and are substantially equal to zero for a substantially horizontal surface. At this time the proportion of gravity recorded by the accelerometers is related, among other things, to the angle from the vertical coordinate (as resolved by an accelerometer such as the ADXL05, from Analog Devices).

$$\gamma_x = \sin^{-1}(Ax/g) \quad (9)$$

$$\gamma_y = \sin^{-1}(Ay/g) \quad (10)$$

In order to assure accurate measurements, the accelerometers employed in the present invention are desired to be properly calibrated. The embodiments described herein may be conveniently calibrated in accordance with the present invention. This follows because gravity g only varies by less than 0.3% throughout the surface of the earth, and provides a substantially constant value in a direction substantially aligned towards the center of the earth. Therefore, an accelerometer employed in accordance with the present invention must generate an acceleration signal substantially equal to gravity g, when the user's foot is resting on a surface. It will be appreciated that an embodiment in accordance with the present invention may be configured so as to advantageously reset the value generated by the accelerometers to substantially represent gravity, g, when the user's foot is resting on a surface. As such, the accelerometers employed in accordance with the present invention may remain substantially calibrated at all times.

Since the accelerometers and rotation sensors are connected to a timing device, their values may be known as a function of time. The horizontal and vertical displacement may then be obtained by integrating by time as they traverse the path:

$$Lx = \int\int ax(t)dt^2 \quad (11)$$

$$Ly = \int\int ay(t)dt^2 \quad (12)$$

$$Lz = \int\int az(t)dt^2 \quad (13)$$

The integration is performed twice to obtain Lx, Ly, Lz shown in the equations. Lz would be zero if the ground remained at the slope of the beginning of the step, and would be significant if a person, for example, climbed a step. To obtain the length of the step, $$L = \sqrt{Lx^2 + Ly^2 + Lz^2} \quad (14)$$

The maximum height H jumped is, $$H = \max(Lz)$$

If $L_z$ is not aligned with the vertical axis, the height jumped can be obtained by resolving its component in the direction of gravity, as described below.

Figure 6:
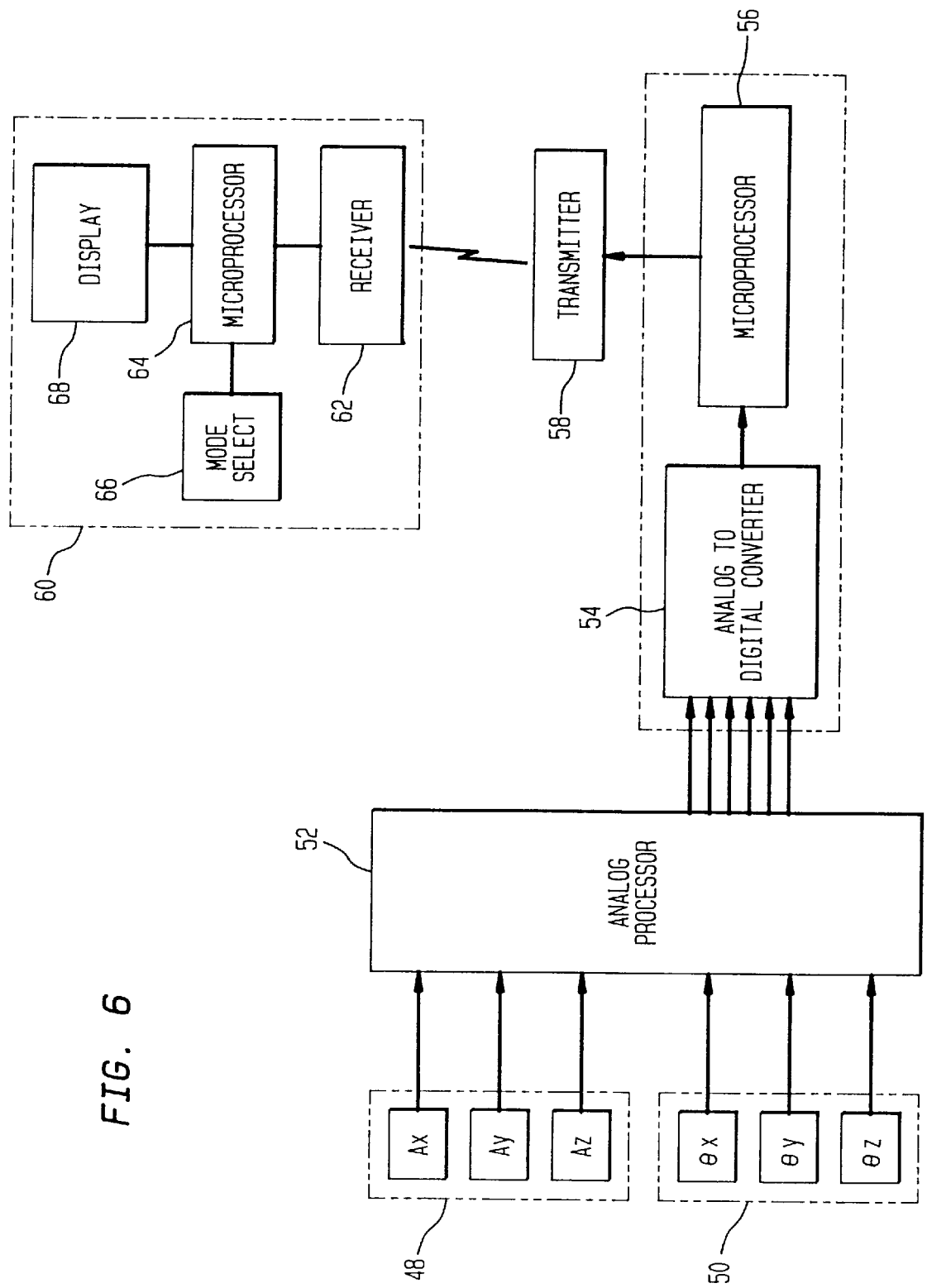
FIG. 6 is a block diagram of the electronic units necessary to solve equations for step length in accordance with the invention.

FIG. 6 is a block diagram of the components employed to solve the equations, although the invention is not limited in scope in this respect. Therefore, any hardware or software system configured to solve the above equations to measure the length of each step and the height jumped may be employed. In FIG. 6, unit 48 may preferably contain the linear accelerometers employed to measure accelerations Ax, Ay and Az and frequency filters (not shown). Such filters may be used to reduce high frequency components in measured acceleration signals. The linear accelerometers are configured to measure accelerations in three dimensions, along the direction of the foot as it travels during each step.

Unit 50 may preferably contain rotational sensors employed to measure θx θy and θz signals. Thus the rotational sensors provide the angle of rotation along each axis of the translational coordinate. The output terminals of units 48 and 50 are coupled to input terminals of a processor 52. Processor 52 may be employed to make the calculations necessary to solve equations 3–5 and 9–10 mentioned above. For example, the sine and cosine of each measured angle may be computed by processor 52. The sine and cosine value signals are then coupled to input terminals of unit 54.

Unit 52 may contain multipliers and adder processors to solve equations 3–5 and 9–10 in analog format. In accordance with another embodiment of the invention, processor 52 may process the received signals digitally by employing an analog to digital converter and a microprocessor that calculates equations 3–5 and 9–10. Yet, in accordance with embodiments of the invention, the output terminals of units 48 and 50 may be coupled directly to a microprocessor 56, via an analog to digital converter 54. Analog to digital converter 54 may be a separate integrated circuit, such as one provided by Linear Technology LTC 1098. In another embodiment of the invention, analog to digital converter 54 may be part of microprocessor 56, such as one provided by Motorola MC68HC11E9.

Microprocessor 56 is preferably configured to measure the distance L traversed during each step and the maximum height H jumped during that step. It will be appreciated that these measurements may be employed in either analog or digital format.

In accordance with one embodiment of the invention, a foot switch (not shown) may be employed so as to reset the accelerometers and rotational sensors contained in units 48 and 50, when the user's shoe contacts the ground. Information relating to the length and height of a step, and the contacts with ground may then be transmitted by transmitter 58 to a remote receiver unit 60. However, the invention is not limited in scope in this respect. For example, instead of a foot switch, the accelerometers or the rotational sensors may be configured to reset themselves, whenever their output signal levels indicate that the user's foot has touched the running surface again.

Unit 60 is the remote device, which may be located in the user's wrist watch, and contains a receiver 62, a microprocessor 64, a mode select switch 66 and a display 68. Transmitter 58 includes a means for encoding the output signals provided by a microprocessor 56 into a transmitted signal. Transmitter 58 may also be of the type already known in the art such as the RF Monolithics model HX2000. Transmitter 58 may operate on any frequency selected and use amplitude or frequency modulation. The transmitted signal from transmitter 58 is received and decoded by receiver 62. Receiver 62 may also be of the type known in the prior art such as the RF Monolithics model RX2010. Receiver 62 may also be selectively tuned to receive the signals of several different transmitters operating on different frequencies so that the performance of several runners may be monitored from a remote location. Microprocessor 64 may be selected from various microprocessors known in the prior art, such as Motorola model MC68HC05L1.

A typical run mode sequence will now be described with reference to FIG. 6. Mode select unit 66 is employed at the start of the run or jog by depressing an appropriate switch, not shown, which is coupled to microprocessor 64 through an input switch control logic interface. As the shoe of the runner comes into contact with the surface, a first output signal is generated by accelerometers contained in unit 48 representing that a foot of the runner is in contact with the surface. Unit 52 begins to calculate the initial orientation of the user's foot along the reference coordinate in accordance with equations (9) and (10).

Thereafter unit 48 generates acceleration signals along the translational coordinates. Rotational sensors contained in unit 50 begin to track the rotation of the user's foot along the translational coordinate system. Thereafter, unit 52 measures instantaneous acceleration of the foot along the reference coordinates as the foot travels in the air and contacts the surface again. Unit 54 receives these acceleration signals and unit 56 calculates the length of each step by integrating the acceleration signals. Unit 56 also calculates the height jumped by obtaining the maximum length measured along the z axis of the reference coordinate system. The output signals are coupled to RF transmitter 58 and transmitted to receiver 62. The signals received by receiver 62 are coupled to microprocessor 64. The microprocessor interface converts the output of a microprocessor to signals suitable to drive display 68.

Speed is continuously calculated by measuring the distance of each step and is instantaneously available for display. Microprocessor 64 also maintains running elapsed time. Microprocessor 64 may be configured to calculate distance traversed by summing the length of all steps taken. It may further be configured to calculate the instantaneous and the average speed of the user. The running elapsed time, the distance traversed and the speed may be selectively displayed on display 68. These values may also be stored in a non-volatile memory (not shown) associated with microprocessor 64 for virtually an indefinite period of time.

For calibration purposes, microprocessor 56 may be desirably configured to monitor the value of signals provided by accelerometers of unit 48. Whenever it is determined that the user's foot is on the running surface, the value of these signals may correspond to gravity, g. If, however, the value of the these signals does not correspond to gravity, g, microprocessor 56 may provide a feedback signal so as to reset the values of the accelerometers to provide a desired signal representing gravity, g.

In the watch mode, microprocessor 64 selectively provides to display 68, normal watch functions such as time of day, date, an alarm signal when a preselected time occurs. Obviously, many modifications and variations of the above preferred embodiment of the invention will become apparent to those skilled in the art from a reading of this disclosure. For example, a less expensive embodiment may be implemented where all electronic components are disposed on the shoe. In that case, there may be no desire for a transmitter and a receiver circuit. It may also be possible to combine the functions performed by microprocessors 56 and 64 into one microprocessor, such as a Motorola model MC68HC05L. In the alternative it is also possible to combine the functions performed by signal processor 52, and microprocessors 56 and 64 into one such microprocessor.

Figure 7:
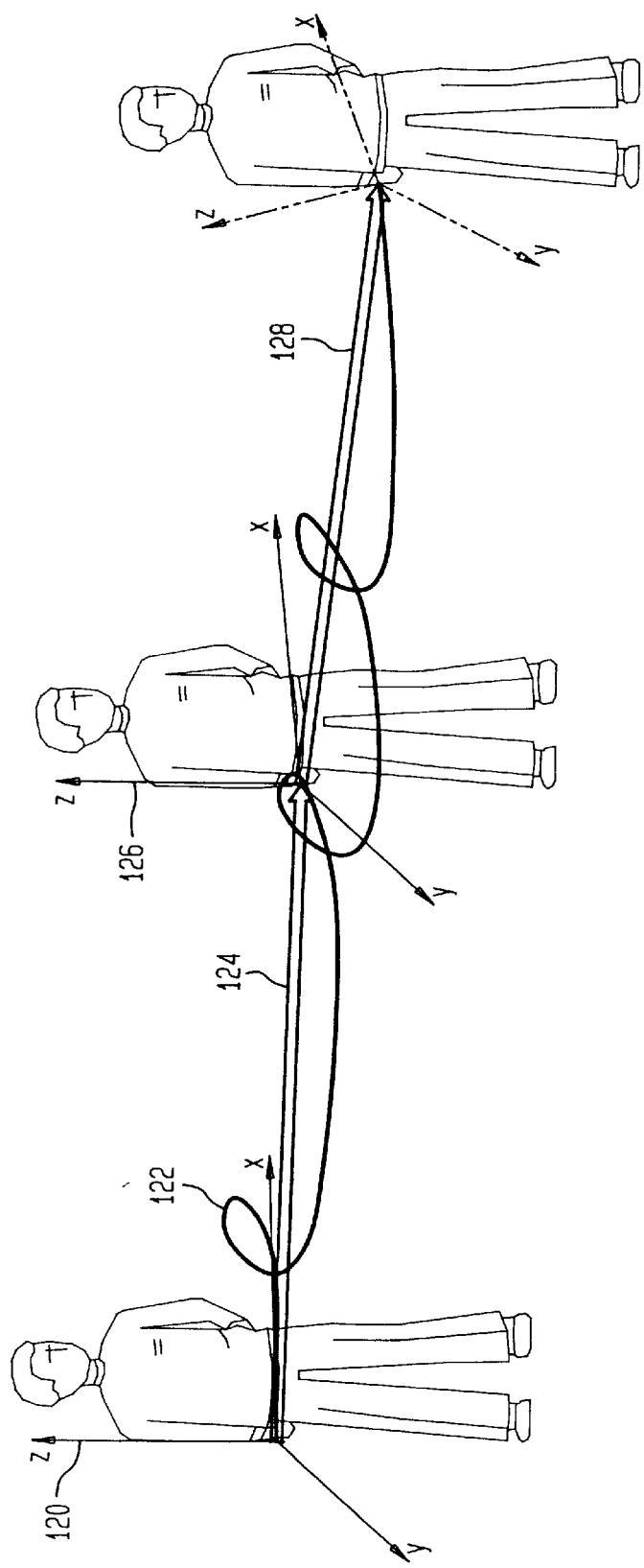
FIG. 7 illustrates the reference frame and a plot of the path of the motion of a wrist during walking or jogging, and the measurement of the distance traveled in accordance with one embodiment of the invention.

As mentioned above, in accordance with other embodiments of the invention, measuring system 10 can be located on parts of the body other than the foot of the user and still achieve the same accuracy in measuring the speed, distance traveled, and the height jumped. For example as discussed above, the measuring system may be employed at the wrist or the waist of the user as discussed hereinafter. FIG. 7 is a plot illustrating an embodiment of the invention employed on the wrist of the user.

A reference coordinate frame 120 is set at the initiation of a cycle, and remains fixed for the duration of the cycle. For the purposes of the present embodiment, a cycle is the period during which a new reference frame is defined and remains fixed. Preferably, the system measures the distance traveled during each cycle. As such, a cycle does not need to be related to the steps of the user, and can include several steps. This reference frame may have a given orientation that is not necessary aligned along the gravitational field.

The motion of the wrist during a couple of cycles is traced by a thin line 122. The linear distance traveled by the wrist at the end of the first cycle is shown as a straight arrow 124. A new cycle is initiated at the same instant, with a new reference coordinate system 126. The linear distance to the position of the wrist at the end of the second cycle is shown as a straight arrow 128. The total distance traveled is the sum of distances for all cycles. The velocity of travel is the distance of the cycle, or several cycles, divided by the time it takes to travel this distance. The height jump is not obtainable with the wrist embodiment because it is not possible to differentiate between the height jumped by the person and the vertical movement of wrist. However, in the embodiment where the measuring system is employed at the waist of the user, the height jumped is also measurable.

Figure 8:
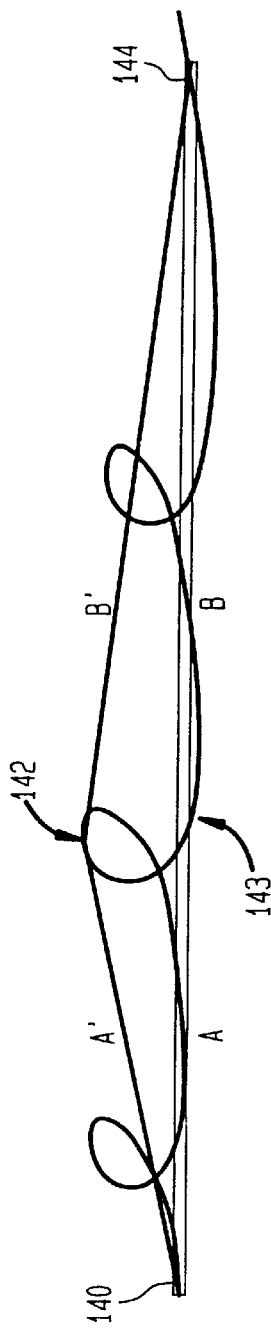
FIG. 8 illustrates a plot that explains possible errors caused by locating the measuring system in the wrist of a user.

The movement of the wrist may cause systematic error due to the fact that the position of the measuring system at the beginning of a cycle may not be the same as its position at the end of a cycle. For example, if the wrist is moving in a circular, sideways, or up and down manner, the measuring system may exhibit error as illustrated in FIG. 8. As illustrated, when the cycle starts with the wrist in position 140, and ends with the wrist in position 142, when it should have been in position 143, then the error is the difference between the distance A and A'. If during the following cycle the wrist ends in position 144, then there is another error caused by the difference between the length B and B'. However, this error is negligible for most applications. For example, if the typical distance between position 142 and 143 is 12 inches, and the lateral distance of a cycle is 200 inches, then the difference between A and A' is 1.1 inches, which is approximately a 0.5% error.

The error caused by erratic motions of the wrist is systematic as the distance between A' is always longer than or equal to A, or B' is always longer than or equal to B. The error depends upon the number of steps taken during a cycle.

Random error may be due to the fact that a cycle begins or ends such that the wrist is forward or behind the person. In such a circumstance the error may be made up in following cycles. Thus a series of cycles is used to calculate overall distance in order to average out random errors. As a result it is desirable to determine the length of a cycle that minimizes systematic errors yet allows enough cycles to average out random error. In one embodiment of the invention, this length is obtained by testing.

Figure 9:
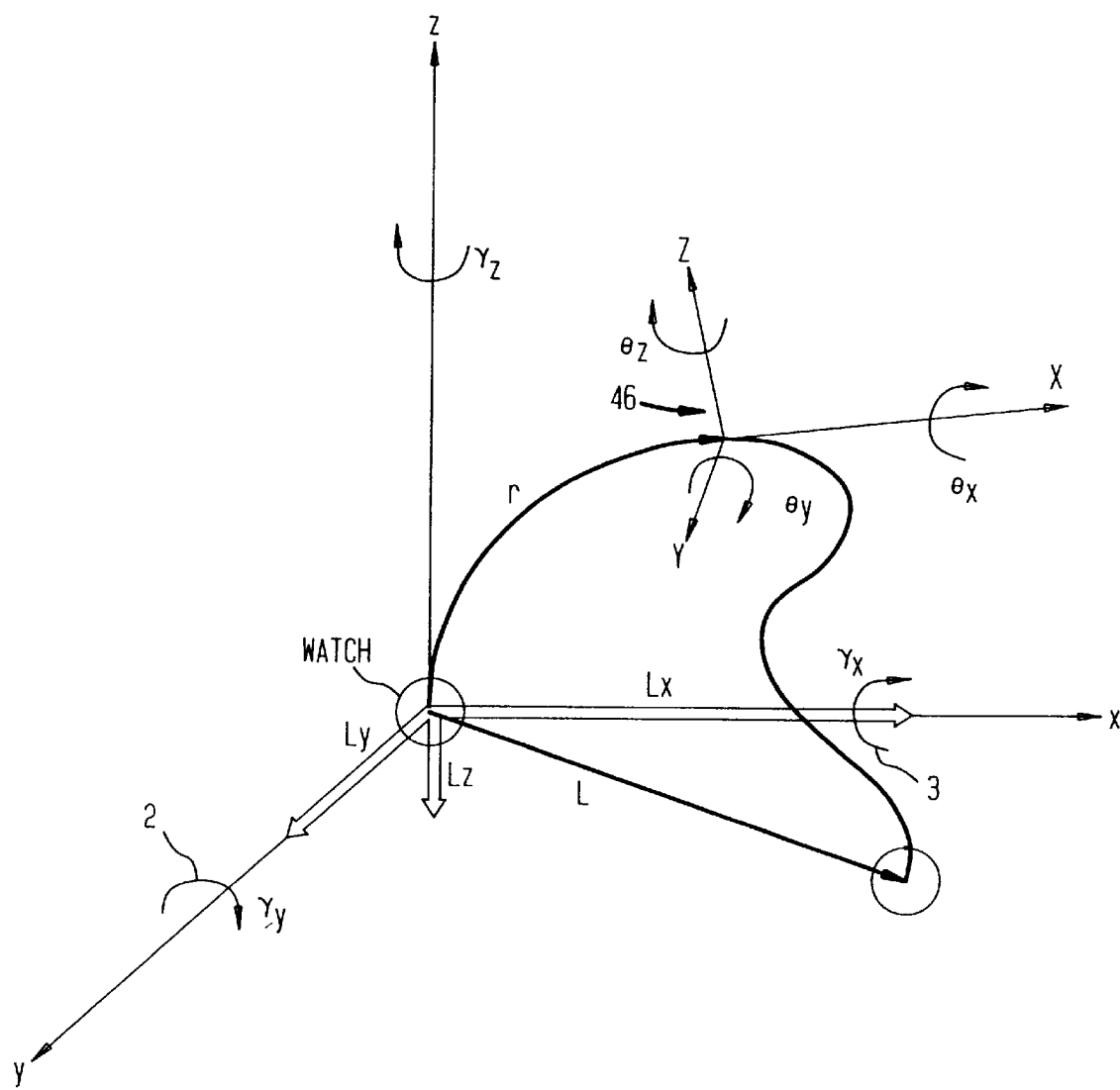
FIG. 9 illustrates the coordinate system utilized to measure the distance traveled by a user employing the measuring system in the wrist or other areas of the body.

FIG. 9 shows exemplary coordinate systems employed to obtain a solution for the distance traveled by a person who employs the measuring system of the present invention at a wrist or a waist. As illustrated, FIG. 9 represents the same parameters as discussed with reference to FIG. 5, except that the distance traveled is measured from the wrist or the waist of the user rather than the shoe of the user. At the initiation of a cycle the reference frame is set along a given orientation. The reference frame remains fixed for the entire period of a cycle.

As mentioned before, a new reference frame is defined at the beginning of each cycle. Preferably, each new cycle begins when the accelerometers are substantially influenced by gravity and not by the acceleration of the measuring device itself. To this end, the components of gravity acting on the three accelerometers of the measuring device at the initiation of each cycle is advantageously the value of the accelerometer readings $A^0x$, $A^0y$, and $A^0z$ due to gravity, such that $$(A^0x)^2+(A^0y)^2+(A^0z)^2=g^2 \tag{16}$$

Furthermore, preferably the velocity of the measuring device at the beginning of each cycle is a constant, which indicates that the accelerations of the measuring device itself is substantially zero, so that the accelerometers are influenced substantially by the gravity and not by the acceleration of the measuring device.

Thus, in accordance with one embodiment of the present invention, the system initiates a new cycle, whenever a predetermined number of velocity samples remain constant. At this time, the orientation of gravity can be determined and used to calculate the height jumped by a person.

As a result the acceleration of the measuring device along its transitional coordinates may be obtained as follows:

$$ax=AxC_1-AyC_2+AzC_3-A^0_x \tag{17}$$

$$ay=AxC_4+AyC_5-AzC_6-A^0_y \tag{18}$$

$$az=-AxC_7+AyCo_8+AzC_9-A^0_z \tag{19}$$

where the coefficients $C_1$–$C_9$ are determined as described for equations 3–5.

The calculation of the length of travel during a cycle follows the description above in reference with FIG. 5. However, the length of lateral motion of a cycle is also measured. The transitional coordinate system moves with the measuring system, such as the watch, and provides a value of Ax, Ay, Az and $\theta_x$, $\theta_y$ and $\theta_z$ for determining the coefficients for equations 17–19. The length traversed by the measuring system is obtained by employing equations 20–22 as follows:

$$Lx= \int ax(t)dt^2+TV^0_x \tag{20}$$

$$Ly= \int ay(t)dt^2+TV^0_y \tag{21}$$

$$Lz= \int az(t)dt^2+TV^0_z \tag{22}$$

The value of accelerations are integrated twice to obtain Lx, Ly, and Lz, shown in equations 20–22, where $V^0_x$, $V^0_y$ and $V^0_z$ are the values of velocity of the sensors at the initiation of a cycle and T is the time of the cycle. The length of a cycle can then be obtained as follows:

$$L = \sqrt{Lx^2 + Ly^2 + Lz^2} \tag{23}$$

The maximum height H jumped is, $$H=\max(Lz)\cdot\hat{g} \tag{24}$$

where $\hat{g}$ is the unit vector aligned with gravity.

It is noted that the system takes into account the effects of gravity at the beginning of each cycle as set forth by equation (16) due to the fact that the accelerometers employed in a preferred embodiment of the invention are forced balance accelerometers that operate based on inertial mass effects. Thus, preferably a distinction is made between the acceleration of the user and outside acceleration due to an external force, such as gravity, acting upon the user. A forced balance accelerometer considers an external force that pulls on the inertial mass in a particular direction as if the user is accelerating in the opposite direction. As a result, the effects of gravity may be considered as if the user is accelerating with the same acceleration substantially equal to effects of gravity.

In accordance with another embodiment of the invention, instead of accelerometers velocity sensors may be employed. For a measuring system that employs a velocity sensor the condition set forth by equation (16) becomes unnecessary. Thus a new cycle may advantageously begin at any time the velocity of the user is constant.

It will be appreciated by those skilled in the art, that the measuring system in accordance with the present invention, may be employed in a variety of applications beyond the use for walking and jogging.

For example a measuring system may be implemented for medical and biomedical applications. As such, a measuring system in accordance with the present invention is used in an orthopedic or a prosthetic device to track the durability of the device over a total distance traveled by the user. For example, in a preferred embodiment patients that undergo hip replacement surgery, employ a measuring system, either internally, for example adjacent to the replaced hip or externally, so as to measure the total distance traveled by a replaced hip. This allows physicians and engineers to collect valuable data relating to the durability and performance of the artificial hips based on the type of material used, various artificial hip designs employed or various surgical techniques used.

In accordance with another embodiment of the invention, measuring systems that operate based on the principles of the present invention are placed on any limb or extremity of a patient to detect and diagnose range of movements of the patient, or range of motion, and compare with normal benchmarks.

In accordance with yet another embodiment of the invention a measuring device is placed in an object, such as a golf ball, in order to conveniently measure the distance and the height traversed by the ball.

In another embodiment of the invention, a plurality of measuring devices may be employed within a moving object so as to measure various movements relating to each measuring device. Values measured by each measuring device may then be combined by a central processor so as to determine the movements of the measuring devices in relation to each other. For example, measuring devices may be attached to a clothing article to create a "smart" clothing article. A user advantageously wears the clothing article. Each measuring device in the clothing article tracks movement, acceleration, distance and speed for further calculations.

In another embodiment of the invention a plurality of measuring devices may be employed by a plurality of persons or objects. Each measuring device transmits information relating to its movement, acceleration, distance and speed to a centralized location so that the movement of a group of persons or objects is advantageously monitored. In addition, when it is necessary to monitor the movement of a group of animals, each measuring device is attached to an animal for further monitoring. Such a system may be advantageous for wild life preservation purposes, or in the alternative, for commercial purposes, such as cattle grazing and so forth.

In another embodiment of the invention, a measuring device operating in accordance with the principles of the present invention may be used for navigational purposes. For example, at the initiation of the system, the user's location coordinates are entered into the measuring device. The measuring device thereafter tracks the location of the movement of the user in relation to the user's initial location.

It should be realized that the invention is not limited to the particular embodiment disclosed, but its scope is intended to be governed only by the scope of the appended claims.

I claim:

1. A system for measuring a speed and distance of an object, said system comprising:

a plurality of accelerometers and rotational sensors disposed in said object said accelerometers configured so as to provide acceleration signals corresponding to accelerations associated with a movement of said object during a plurality of measurement cycles, said rotational sensors configured so as to provide angular signals corresponding to an angle of said object about an axis of a three dimensional translational coordinate; and a calculator coupled to said accelerometers and said rotational sensors configured so as to receive said acceleration signals and said angular signals, said calculator adapted to measure a distance traversed and the speed of said object during each of said measurement cycles, wherein each measurement cycle begins when said object has a constant velocity.

2. The system in accordance with claim 1, wherein said calculator further measures a height jumped by said object.

3. The system in accordance with claim 2 further comprising a processor adapted to receive signals corresponding to said distance and said height jumped so as to calculate a total length traversed by said object and generate a corresponding output distance signal, said processor further adapted to generate a height jumped signal.

4. The system in accordance with claim 3, wherein said processor further calculates an instantaneous and an average speed of said object and generates a corresponding output speed signal.

5. The system in accordance with claim 4, wherein said processor includes a timer means for producing output time signals representing a date, a time of day and a time elapsed from a predetermined time, said display means further comprising means for displaying said date, said time of day and said elapsed time in accordance with said output time signals.

6. The system in accordance with claim 4 wherein said processor further comprises means for timing a running elapsed time and generating a signal representing a time elapsed from the beginning of a run.

7. The system in accordance with claim 6 wherein said output speed signal, said running elapsed time signal, said output distance signal and said height jumped signal are stored for a virtually indefinite period of time and selectively displayed.

8. A system for measuring a speed and distance of an object over a plurality of measurement cycles, said system comprising:

an accelerometer unit disposed in said object, said accelerometer unit containing a plurality of accelerometers configured to measure acceleration associated with a movement of said object along a translational coordinate defined by the movement of said object, said accelerometers further configured to generate acceleration signals corresponding to said measured accelerations;

a rotational sensor unit disposed in said object, said rotational sensor unit containing a plurality of rotational sensors configured so as to provide angular signals corresponding to an angle of rotation of said object about each one of said translational coordinates;

a first calculator unit coupled to said accelerometer unit and said rotational sensor unit configured so as to receive said acceleration signals and said angular signals, said calculator adapted to measure instantaneous accelerations of said object with respect to a reference coordinate defined by said object at the initiation of each one of said measurement cycles wherein each of said measurement cycles initiates when velocity of said object is constant;

a second calculator unit coupled to said first calculator unit configured so as to receive said instantaneous accelerations, said second calculator adapted to measure a length traveled during each one of said cycles and a height jumped by said object.

9. The system in accordance with claim 8, wherein said accelerometer unit contains three accelerometers each configured to measure accelerations $A_x$, $A_y$, and $A_z$ along X,Y, and Z coordinates of said translational coordinate system.

10. The system in accordance with claim 9, wherein said rotational sensor unit contains three rotational sensors each configured to measure angular signals θx, θy and θz corresponding to the angle of rotation of said object about a respective X, Y, and Z axis of said translational coordinate system.

11. The system in accordance with claim 10, wherein each one of said cycles is initiated when a velocity of said object is constant and said accelerometers are substantially influenced by gravity such that $$(A^0_x)^2+(A^0_y)^2+(A^0_z)^2=g^2$$

where $A^0_x$, $A^0_y$, and $A^0_z$ are accelerations values provided by the accelerometers at the beginning of each cycle.

12. The system in accordance with claim 11, wherein said first calculator derives acceleration signals along said reference coordinate system in accordance with $$ax=AxC_1-AyC_2+AzC_3-A^0_x$$

$$ay=AxC_4+AyC_5-AzC_6-A^0_y$$

$$az=-AxC_7+AyC_8+AzC_9-A^0_z$$

where $C_1$–$C_9$ are transformation coefficients and ax is acceleration along an x axis of said reference coordinate, ay is acceleration along a y axis of said reference coordinate, az is acceleration along a z axis of said reference coordinate.

13. The system in accordance with claim 12, wherein said accelerometers are configured to be calibrated at the beginning of each cycle.

14. The system in accordance with claim 12, wherein said second calculator derives a length of each step L and a height H jumped during each step in accordance with $$Lx= ax(t)dt^2+TV^0_x$$

$$Ly= ay(t)dt^2+TV^0_y$$

$$Lz= az(t)dt^2+TV^0_z$$

$$L = \sqrt{Lx^2 + Ly^2 + Lz^2}$$

$$H=\max(Lz)\cdot \hat{g}$$

where $V^0_x$, $V^0_y$ and $V^0_z$ are values of velocity at the initiation of a cycle and T is a time of the cycle and where Lx, Ly and Lz are respectively a length of the object measured along the reference frame coordinates, during each cycle and $\hat{g}$ is a unit vector aligned in the direction of gravity.

15. A method for measuring a distance traveled by an object over a plurality of measurement cycles comprising the steps of:

measuring an acceleration associated with a movement of said object along a translational coordinate defined by the movement of said object;

measuring an angle of rotation of said object about each one of said translational coordinates;

calculating instantaneous accelerations of said object with respect to a reference coordinate defined by said object at the beginning of each one of said cycles, wherein each one of said measurement cycles begin when velocity of said object is constant; and calculating a length traveled by said object and a height jumped by said object in accordance with said calculated instantaneous accelerations.

16. The method in accordance with claim 15, further comprising the step of repeating said measuring and calculating steps at the initiation of each cycle.

17. The method in accordance with claim 16, further comprising the step of accumulating each calculated length over a cycle to measure a total distance traveled by said object.

18. The method in accordance with claim 17, further comprising the step of calculating an instantaneous and an average speed of said object.

19. A system for measuring over a plurality of measurement cycles a range of motion of a medical device over a distance traveled by a user, said system comprising:

an accelerometer unit disposed in said medical device, said accelerometer unit containing a plurality of accelerometers configured to measure the an acceleration associated with a movement of said medical device along a translational coordinate defined by the movement of said medical device, said accelerometers further configured to generate acceleration signals corresponding to said measured accelerations;

a rotational sensor unit disposed in said medical device, said rotational sensor unit containing a plurality of rotational sensors configured so as to provide angular signals corresponding to an angle of rotation of said medical device about each one of said translational coordinates;

a first calculator unit coupled to said accelerometer unit and said rotational sensor unit configured so as to receive said acceleration signals and said angular signals, said calculator adapted to measure instantaneous accelerations of said medical device with respect to a reference coordinate defined by said medical device at the initiation of each one of said plurality of measurement cycles, wherein each measurement cycle initiates when said device has a constant velocity; and a second calculator unit coupled to said first calculator unit configured so as to receive said instantaneous accelerations, said second calculator adapted to measure a range of motion traveled during each one of said cycles by said medical device.

20. The system of claim 19, wherein said medical device is a prosthetic device, and said second calculator unit measures a total distance traveled by said prosthetic device.

21. The system of claim 19, wherein said medical device is an orthopedic device.

22. A method for measuring over a plurality of measurement cycles a range of motion of a medical device over a distance traveled by a user, comprising the steps of;

measuring an acceleration associated with a movement of said medical device along a translational coordinate defined by the movement of said medical device;

measuring an angle of rotation of said medical device about each one of said translational coordinates;

calculating instantaneous accelerations of said medical device with respect to a reference coordinate defined by said medical device at the beginning of each one of said plurality of measurement cycles, wherein each measurement cycle begins when said device has a constant velocity; and calculating the range of motion traveled by said medical device in accordance with said calculated instantaneous accelerations.

23. A system for detecting and measuring over a plurality of measurement cycles a distance and a height traversed by a ball, said system comprising;

an accelerometer unit disposed in said ball, said accelerometer unit containing a plurality of accelerometers configured to measure an acceleration associated with a movement of said ball along a translational coordinate defined by the movement of said ball, said accelerometers further configured to generate acceleration signals corresponding to said measured accelerations;

a rotational sensor unit disposed in said ball, said rotational sensor unit containing a plurality of rotational sensors configured so as to provide angular signals corresponding to an angle of rotation of said ball about each one of said translational coordinates;

a first calculator unit coupled to said accelerometer unit and said rotational sensor unit configured so as to receive said acceleration signals and said angular signals, said calculator adapted to measure instantaneous accelerations of said ball with respect to a reference coordinate defined by said ball at the initiation of each one of a plurality of measurement cycles, wherein each of said measurement cycles initiates when velocity of said ball is constant; and a second calculator unit coupled to said first calculator unit configured so as to receive said instantaneous accelerations, said second calculator adapted to measure a length and height traversed by said ball during each one of said cycles.

24. The system according to claim 23, further comprising a display unit for displaying data generated by one of said first and second calculators.

25. A system for monitoring the movement of a group of moving objects over a plurality of measurement cycles, said system comprising:

an accelerometer unit disposed in each one of said objects of said group, said accelerometer unit containing a plurality of accelerometers configured to measure an acceleration associated with movement of said group along a translational coordinate defined by the movement of said group, said accelerometers further configured to generate acceleration signals corresponding to said measured accelerations;

a rotational sensor unit disposed in each one of said objects of said group, said rotational sensor unit containing a plurality of rotational sensors configured so as to provide angular signals corresponding to an angle of rotation of said group about each one of said translational coordinates;

a first calculator unit coupled to said accelerometer unit and said rotational sensor unit configured so as to receive said acceleration signals and said angular signals, said calculator adapted to measure instantaneous accelerations of each one of said objects of said group with respect to a reference coordinate defined by a corresponding object of said group at the initiation of each one of a plurality of measurement cycles, wherein each measurement cycle for each object in said group initiates when said object has a constant velocity; and a second calculator unit coupled to said first calculator unit configured so as to receive said instantaneous accelerations, said second calculator adapted to measure a range of motion traveled during each one of said cycles by each one of said objects of said group.

26. The system according to claim 25, further comprising a display unit for displaying the range of motion of each one of said objects of said group.

27. The system according to claim 25, wherein said group of objects comprises sensors disposed on animals.

28. A system of navigation comprising:

an accelerometer unit disposed on a user, said accelerometer unit containing a plurality of accelerometers configured to measure an acceleration associated with a movement of said user along a translational coordinate defined by the movement of said user, said accelerometers further configured to generate acceleration signals corresponding to said measured accelerations;

a rotational sensor unit disposed on said user, said rotational sensor unit containing a plurality of rotational sensors configured so as to provide angular signals corresponding to an angle of rotation of said user about each one of said translational coordinates;

a first calculator unit coupled to said accelerometer unit and said rotational sensor unit configured so as to receive said acceleration signals and said angular signals, said calculator adapted to measure instantaneous accelerations of said user with respect to a reference coordinate defined by said user at the initiation of each one of a plurality of measurement cycles, wherein each measurement cycle initiates when said user has a constant velocity; and a second calculator unit coupled to said first calculator unit configured so as to receive said instantaneous accelerations, said second calculator adapted to track a location of the movement of the user in relation to the reference coordinate.

29. The system according to claim 28, further comprising a display unit for displaying the data generated by one of said first and second calculators.

30. A method of navigation, comprising the steps of:

measuring an acceleration associated with a movement of a user along a translational coordinate defined by the movement of said user;

measuring an angle of rotation of said user about each one of said translational coordinates;

calculating instantaneous accelerations of said user with respect to a reference coordinate defined by said user at the beginning of each one of a plurality of measurement cycles, wherein each of said measurement cycles being when said user has a constant velocity; and tracking the location of movement of said user in accordance with said calculated instantaneous accelerations.

31. The system in accordance with claim 1 wherein at initiation of each one of said cycles said acceleration signals correspond substantially to effects of gravity and during each one of said measurement cycles said system substantially subtracts acceleration signals received at initiation of each one of said cycles so as to eliminate errors caused by influence of gravity on said system.

32. The system in accordance with claim 8 wherein at initiation of each one of said cycles said acceleration signals correspond substantially to effects of gravity and during each one of said measurement cycles said system substantially subtracts acceleration signals received at initiation of each one of said cycles so as to eliminate errors caused by influence of gravity on said system.

33. The method in accordance with claim 15 wherein said method farther comprises the step of subtracting acceleration signals received at initiation of each one of said cycles so as to eliminate errors caused by influenced of gravity.

34. The system in accordance with claim 19, wherein at initiation of each one of said cycles said acceleration signals correspond substantially to effects of gravity and during each one of said measurement cycles said system substantially subtracts acceleration signals received at initiation of each one of said cycles so as to eliminate errors caused by influence of gravity on said system.

35. The system in accordance with claim 23, wherein at initiation of each one of said cycles said acceleration signals correspond substantially to effects of gravity and during each one of said measurement cycles said system substantially subtracts acceleration signals received at initiation of each one of said cycles so as to eliminate errors caused by influence of gravity on said system.

* * * * *